US007799768B2

(12) United States Patent
O'Neill et al.

(10) Patent No.: US 7,799,768 B2
(45) Date of Patent: Sep. 21, 2010

(54) POLYMORPHS OF 3-O-(3',3'-DIMETHYLSUCCINYL)BETULINIC ACID DI-N-METHYL-D-GLUCAMINE

(75) Inventors: Mike H. O'Neill, Painesville, OH (US); Gary G. Sweetapple, Painesville, OH (US); Randall M. Walker, Willoughby, OH (US); Arndt Hausherr, Mainz (DE); Gunter Koch, Schwabenheim (DE); David E. Martin, Gaithersburg, MD (US)

(73) Assignee: Myrexis, Inc., Salt Lake City, UT (US)

( * ) Notice: Subject to any disclaimer, the term of this patent is extended or adjusted under 35 U.S.C. 154(b) by 894 days.

(21) Appl. No.: 11/401,960

(22) Filed: Apr. 12, 2006

(65) Prior Publication Data

US 2006/0252704 A1 Nov. 9, 2006

Related U.S. Application Data

(60) Provisional application No. 60/670,227, filed on Apr. 12, 2005.

(51) Int. Cl.
*A61K 31/56* (2006.01)
*C07J 53/00* (2006.01)
(52) U.S. Cl. ...................................... 514/169; 552/169
(58) Field of Classification Search ........................ None
See application file for complete search history.

(56) References Cited

U.S. PATENT DOCUMENTS

| | | | |
|---|---|---|---|
| 5,468,888 A | 11/1995 | Bouboutou et al. | |
| 5,624,914 A | 4/1997 | Patel et al. | |
| 5,679,828 A | 10/1997 | Lee et al. | |
| 5,776,912 A | 7/1998 | Patel et al. | |
| 6,043,245 A | 3/2000 | Bennett et al. | |
| 6,147,077 A | 11/2000 | Koch et al. | |
| 6,172,110 B1 | 1/2001 | Lee et al. | |
| 6,670,345 B1 | 12/2003 | Ramadoss et al. | |
| 2003/0171374 A1* | 9/2003 | Kukla et al. ............... | 514/235.8 |
| 2004/0131629 A1 | 7/2004 | Allaway et al. | |
| 2005/0020548 A1 | 1/2005 | Allaway et al. | |
| 2005/0148561 A1 | 7/2005 | Wild et al. | |
| 2005/0239748 A1 | 10/2005 | Power et al. | |
| 2006/0205697 A1 | 9/2006 | Robinson et al. | |
| 2007/0203103 A1 | 8/2007 | Hemp et al. | |

FOREIGN PATENT DOCUMENTS

| | | |
|---|---|---|
| GB | 1415601 | 11/1975 |
| JP | 1-143832 A | 6/1989 |
| JP | 2003-113081 | 4/2003 |
| RU | 2 174 982 C2 | 10/2001 |
| WO | WO 95/04526 A1 | 2/1995 |
| WO | WO 96/39033 A1 | 12/1996 |
| WO | WO 00/59492 A2 | 10/2000 |
| WO | WO 02/26761 A1 | 4/2002 |
| WO | WO 2005/090380 A1 | 9/2005 |

OTHER PUBLICATIONS

Rusmawati, W.M.W., et al., "Solubility of Betulinic Acid in the Microemulsion System of Methyl Acetate/Tween 80:BRIJ 30/$H_2O$," *Orient. J. Chem.* 16:393-398, Oriental Scientific Publishing Company (2001).
Son, L.B., et al., "The Synthesis of Betulinic Acid from Betulin and Its Solubilization with Liposomes," *Bioorgan. Khim.* 24:787-793, Nauka (1998).
Tietze, L.F., et al., "Synthesis of [13C]- and [2H]Betulin for Biological Transformations," *Liebigs Ann. Chem.* (12):1245-1249, Verlag Chemie (1991).
Supplementary European Search Report for International Application No. PCT/US2006/013640, European Patent Office, Munich, Germany, mailed on Apr. 3, 2008.
Dalgleish, A,G., et al., "The CD4 (T4) antigen is an essential component of the receptor for the AIDS retrovirus," *Nature* 312:763-767, Macmillan Journals Ltd. (1984).
Fujioka, T., et al., "Anti-AIDS Agents, 11. Betulinic Acid and Platanic Acid as Anti-HIV Principles from *Syzigium claviflorum*, and the Anti-HIV Activity of Structurally Related Triterpenoids," *J. Nat. Prod.* 57:243-247, The American Society of Pharmacognosy at Chicago College of Pharmacy (1994).
Kashiwada, Y., et al., "Synthesis and Anti-HIV Activity of 3-Alkylamido-3-deoxy-betulinic Acid Derivatives," *Chem. Pharm. Bull.* 48:1387-1390, Pharmaceutical Society of Japan (2000).
Kashiwada, Y., et al., "Betulinic Acid and Dihydrobetulinic Acid Derivatives as Potent Anti-HIV Agents," *J. Med. Chem.* 39:1016-1017, American Chemical Society (1996).
Kashiwada, Y., et al., "Anti-AIDS Agents. 30. Anti-HIV Activity of Oleanolic Acid, Pomolic Acid, and Structurally Related Triterpenoids," *J. Nat. Prod.* 61:1090-1095, American Chemical Society (1998).
Kashiwada, Y., et al., "Anti-AIDS Agents 38. Anti-HIV Activity of 3-O-Acyl Ursolic Acid Derivatives," *J. Nat. Prod.* 63:1619-1622, American Chemical Society (2000).
Pokrovskii, A.G., et al., "Synthesis of derivatives of plant triterpenes and study of their antiviral and immunostimulating activity," *Khimiya v Interesakh Ustoichivogo Razvitiya* 9:485-491, Siberian Branch of the Russian Academy of Sciences (2001).
Zhu, Y.-M., et al., "Synthesis and Anti-HIV Activity of Oleanolic Acid Derivatives," *Bioorg. Med. Chem. Lett.* 11:3115-3118, Elsevier Science Ltd. (2001).
Database CAPLUS on STN, Chemical abstracts, Accession No. 2001:183502, Rusmawati, W.M.W., et al., "Solubility of betulinic acid in the microemulsion system of methyl acetate/Tween 80:Brij 30/H2O," *Oriental Journal of Chemistry* 16(3):393-398 (2000), Answer 5 of 12 Caplus.

(Continued)

*Primary Examiner*—Elli Peselev
(74) *Attorney, Agent, or Firm*—Herbert L. Ley, III; I.P. Group; Myrexis, Inc.

(57) ABSTRACT

The present invention relates to crystalline polymorphs of 3-O-(3',3'-dimethylsuccinyl)betulinic acid di-N-methyl-D-glucamine salt ("DSB•2NMG"), pharmaceutical compositions of the same and use of the same as an active pharmaceutical agent in the treatment of HIV related disorders.

28 Claims, 10 Drawing Sheets

OTHER PUBLICATIONS

Figure 1:
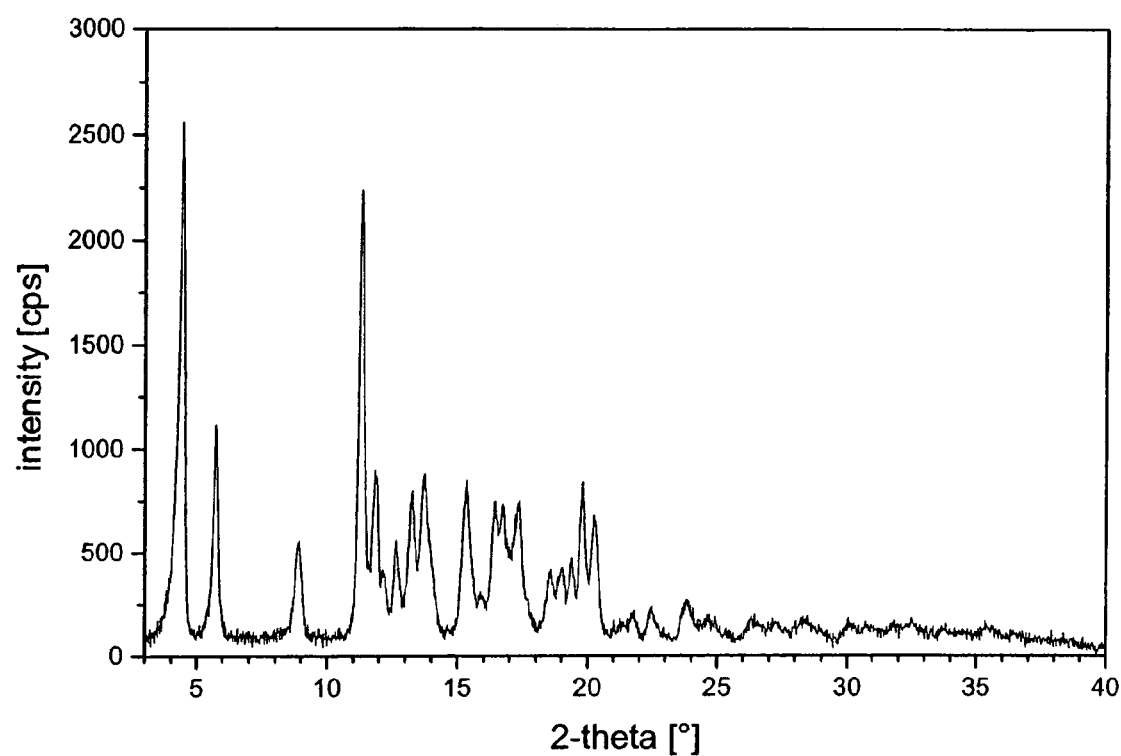

Database CAPLUS on STN, Chemical abstracts, Accession No. 1999:287148, Son, L.B., et al., "The synthesis Betulinic acid from betulin and its solubilization with liposomes," *Bioorganicheskaya Khimiya* 24 (10):787-793 (1998), Answer 8 of 12 Caplus.

Database CAPLUS on STN, Chemical abstracts, Accession No. 1992:59659, Tietze, L.F., et al., "Synthesis of [13C]- and [2H]betulin for biological transformations," *Liebigs Annalen der Chemie* (12):1245-1249 (1991), Answer 11 of 12 Caplus.

Dialog File No. 351, Accession No. 7938971, Derwent WPI English language abstract of JP 1-143832 A (listed on accompanying PTO/SB/08A as document FP2), 1989.

International Search Report for International Application No. PCT/US06/13640, United States Patent and Trademark Office, Alexandria, VA, mailed on Jan. 22, 2007.

Patent Abstracts of Japan, English language abstract of JP 2003-113081 (listed on accompanying PTO/SB/08A as document FP7).

STN/Easy CAplus Database, Accession No. 2001:541179, English language abstract of document NPL7, Pokrovskii, A.G., et al., "Synthesis of derivatives of plant triterpenes and study of their antiviral and immunostimulating activity," *Khimiya v Interesakh Ustoichivogo Razvitiya* 9:485-491, Siberian Branch of the Russian Academy of Sciences (2001).

* cited by examiner

POLYMORPHS OF 3-O-(3',3'-DIMETHYLSUCCINYL)BETULINIC ACID DI-N-METHYL-D-GLUCAMINE

This application is a non-provisional application of U.S. Provisional Application No. 60/670,227, filed Apr. 12, 2005, the entire disclosure of which is herein incorporated by reference.

BACKGROUND OF THE INVENTION

1. Field of the Invention

The present invention relates to the solid state chemistry of 3-O-(3',3'-dimethylsuccinyl)betulinic acid di-N-methyl-D-glucamine salt ("DSB•2NMG") and its use as an active pharmaceutical agent.

2. Background Art

3-O-(3',3'-dimethylsuccinyl)betulinic acid di-N-methyl-D-glucamine ("DSB•2NMG", shown below) is useful in the treatment of HIV and related diseases.

Compound A

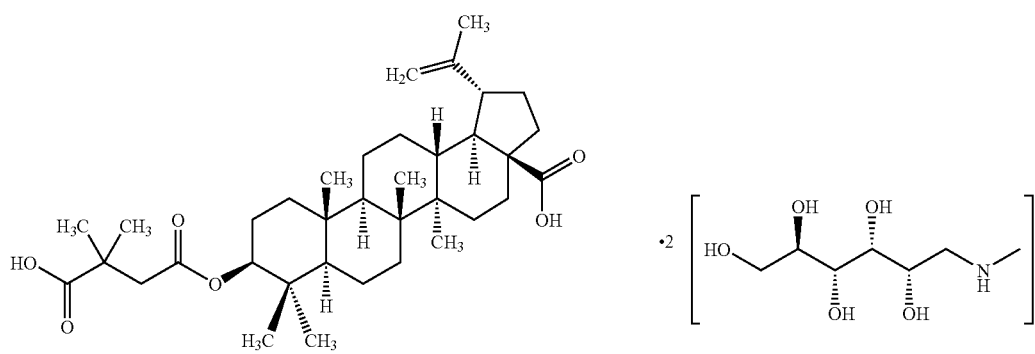

U.S. Patent Application No. 60/413,451 discloses 3,3-dimethylsuccinyl betulin and is herein incorporated by reference. Zhu, Y-M. et al., *Bioorg. Chem Lett.* 11:3115-3118 (2001); Kashiwada Y. et al., *J. Nat. Prod.* 61:1090-1095 (1998); Kashiwada Y. et al., *J. Nat. Prod.* 63:1619-1622 (2000); and Kashiwada Y. et al., *Chem. Pharm. Bull.* 48:1387-1390 (2000) disclose dimethylsuccinyl betulinic acid ("DSB") and dimethylsuccinyl oleanolic acid. Esterification of the 3' carbon of betulin with succinic acid produced a compound capable of inhibiting HIV-1 activity (Pokrovskii, A. G. et al., *Gos. Nauchnyi Tsentr Virusol. Biotekhnol. "Vector,"* 9:485-491 (2001)).

U.S. patent application Ser. No. 11/081,802 herein incorporated by reference discloses salts of DSB, including N-methyl-D-glucamine salts, their preparation, pharmaceutical compositions thereof, and methods of use thereof in the treatment of HIV. The preparation of DSB•2NMG described in Ser. No. 11/081,802 involves the slow addition of diethyl ether to a methanolic solution of DSB•2NMG to produce a white solid. U.S. patent application Ser. No. 11/081,802 describes certain DSB•2NMG as crystalline, however, upon further spectral inspection, it has been determined that material produced in accordance with the procedure in paragraph [0088] of Ser. No. 11/081,802 (or paragraph [0074] of U.S. Publication No. US 2005/0239748) is actually amorphous DSB•2NMG as confirmed by x-ray powder diffraction data depicted herein.

As crystalline compounds demonstrate differing chemical and physical properties relative to amorphous compounds, the identification of crystalline forms of DSB•2NMG would represent an advance in the pharmaceutical arts. Synthetic processes useful to prepare such crystalline forms of DSB•2NMG would represent a further advance in the art. Methods of using such crystalline forms of DSB•2NMG would represent yet another advance in the art.

BRIEF SUMMARY OF THE INVENTION

There are now provided two new crystal forms of DSB•2NMG, solvates thereof, processes for preparing said forms of DSB•2NMG, pharmaceutical compositions comprising said forms of DSB•2NMG, and methods of treatment comprising administration of said forms of DSB•2NMG.

In one aspect the present invention provides crystalline DSB•2NMG Form I. DSB•2NMG Form I has substantially the XRPD pattern shown in FIG. 1 and Table 1.

TABLE 1

X-Ray Diffraction Pattern for DSB.2NMG Form I

| 2-theta | $I/I_0$ (x100) |
|---|---|
| 4.43 | 100 |
| 5.74 | 43 |
| 8.91 | 20 |
| 11.32 | 87 |
| 11.88 | 33 |
| 12.17 | 14 |
| 12.64 | 21 |
| 13.23 | 29 |
| 13.72 | 33 |
| 15.33 | 31 |
| 15.89 | 11 |
| 16.42 | 27 |
| 16.72 | 27 |
| 17.32 | 27 |
| 18.57 | 14 |
| 19.01 | 15 |
| 19.40 | 16 |
| 19.80 | 30 |
| 20.26 | 25 |
| 21.02 | 5 |
| 21.79 | 6 |
| 22.50 | 8 |
| 23.85 | 9 |

In another aspect the present invention provides a process for initiating crystallization of DSB•2NMG Form I comprising:
(a) preparing a solution of DSB•2NMG in a first suitable solvent;
(b) heating the solution to an elevated temperature;
(c) adjusting the temperature of the solution to a growth temperature; DSB•2NMG Form I; and
(d) isolating crystalline DSB•2NMG Form I.

A further aspect of the present invention provides a process for initiating crystallization of DSB•2NMG Form I comprising the steps of the preceding process in order from (a) through (d). A still further aspect of the invention provides a process for initiating crystallization of DSB•2NMG Form I, comprising less than all of steps (a)-(d).

Figure 4:
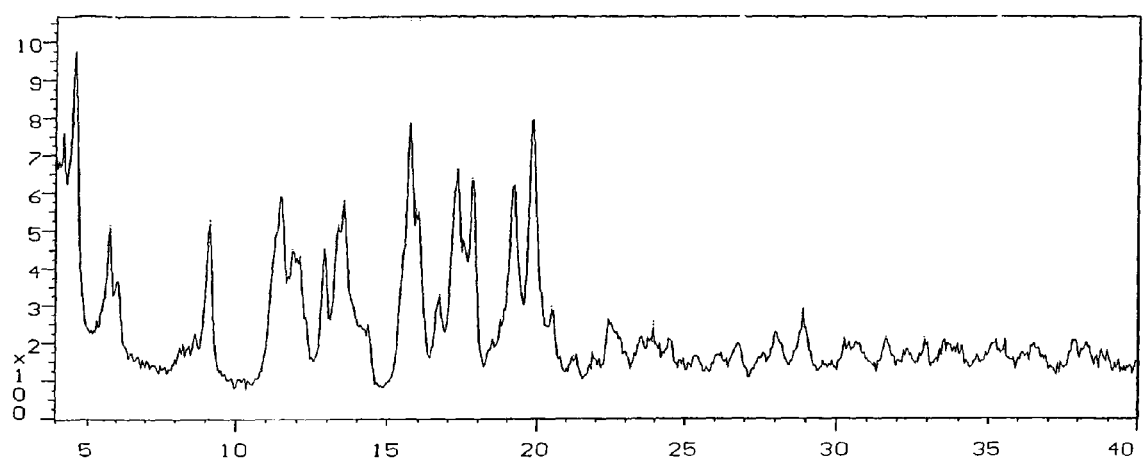

A further aspect of the present invention provides DSB•2NMG Form I having substantially the XRPD pattern shown in FIG. 4, and obtained by annealing.

Figure 5:
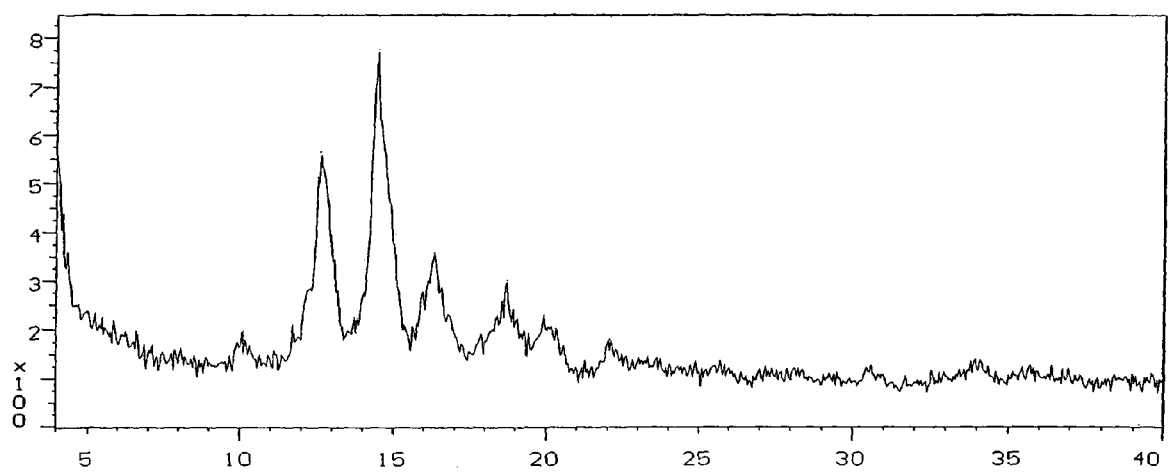

In another aspect the present invention provides crystalline DSB•2NMG Form II, having substantially the XRPD pattern shown in FIG. 5. This particular crystal form is characterized by the X-ray diffraction pattern shown in Table 2.

TABLE 2

X-Ray Diffraction Pattern for DSB.2NMG Form II

| 2-theta | I/I$_0$ (x100) |
|---|---|
| 12.60 | 62 |
| 14.45 | 100 |
| 16.30 | 32 |
| 18.70 | 23 |
| 19.90 | 18 |
| 22.05 | 7 |
| 30.45 | 5 |
| 33.95 | 6 |

Crystalline DSB•2NMG Form II, can be prepared by a process comprising:
(a) preparing a saturated solution of DSB•2NMG in methyl ethyl ketone;
(b) heating the solution to a temperature above the saturation temperature;
(c) adjusting the temperature of the solution to a growth temperature;
(d) evaporating methyl ethyl ketone; and
(e) isolating crystalline DSB•2NMG Form II.

In another aspect, the present invention provides amorphous DSB•2NMG. Amorphous DSB•2NMG can be prepared by dissolving DSB•2NMG in a solvent to form a solution of DSB•2NMG and spray drying the solution.

In another aspect, the present invention provides pharmaceutical compositions of DSB•2NMG polymorphs and their methods of administration.

BRIEF DESCRIPTION OF THE DRAWINGS/FIGURES

Figure 2:
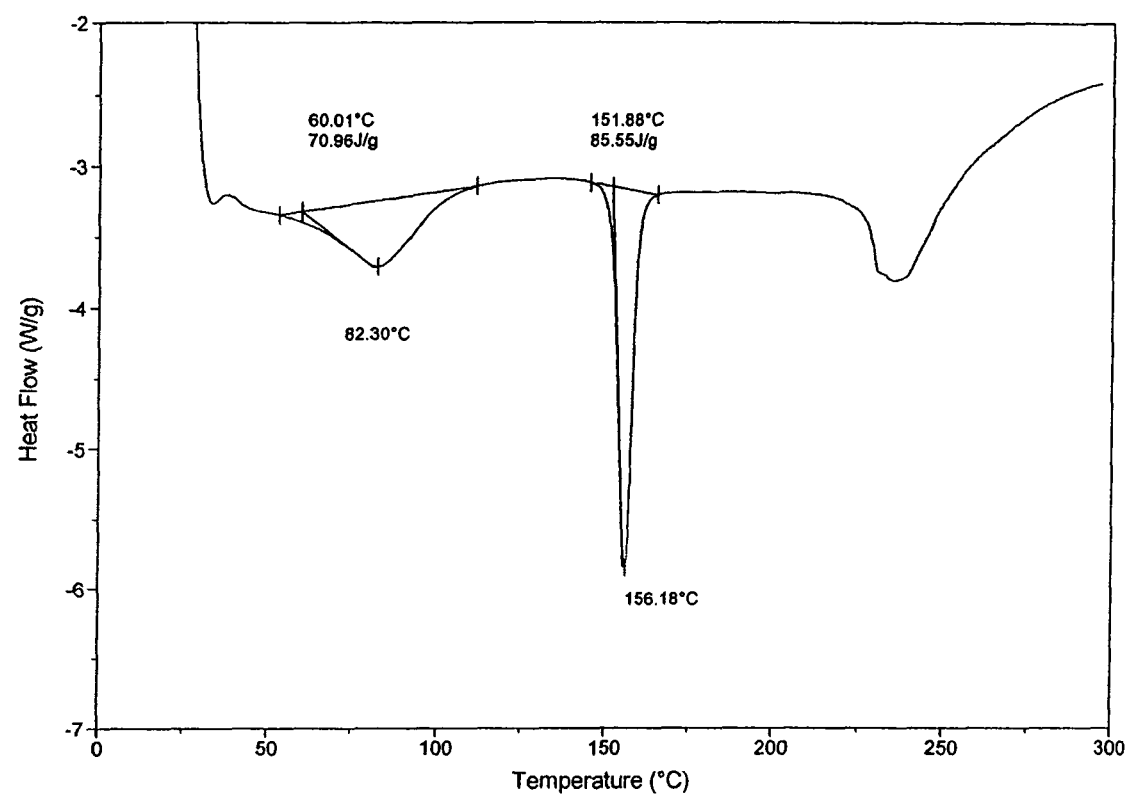
Figure 3:
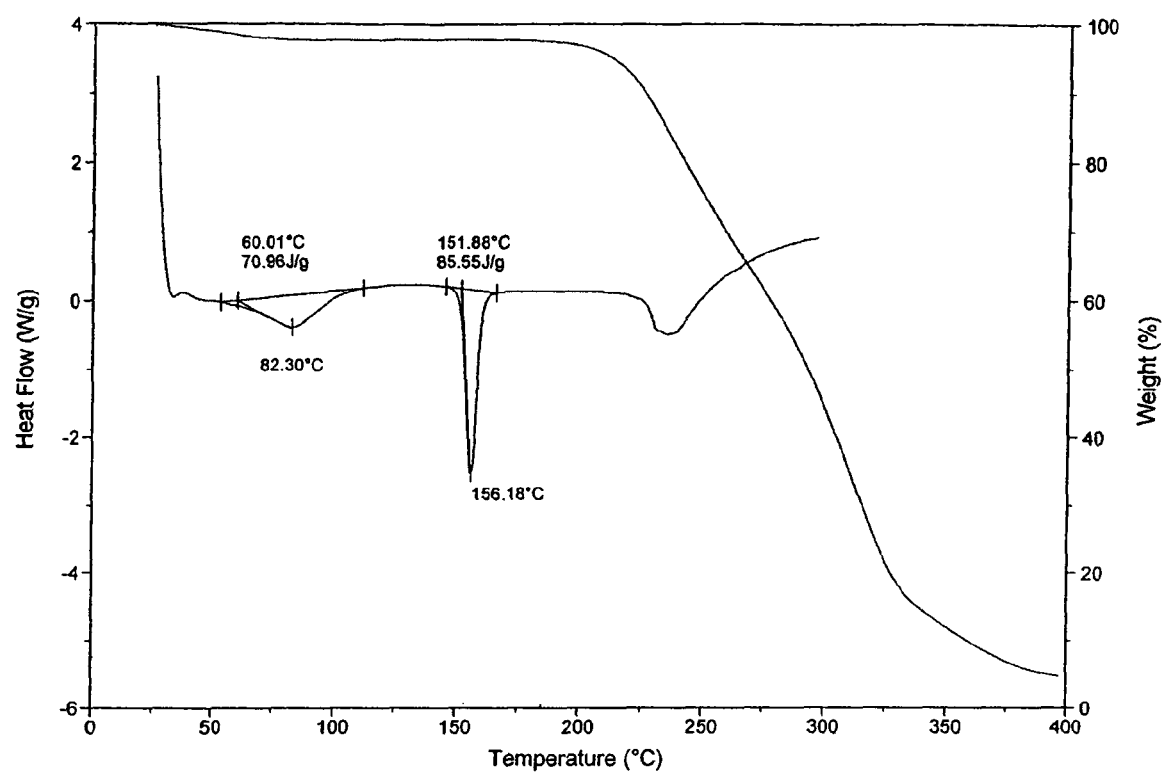
Figure 6:
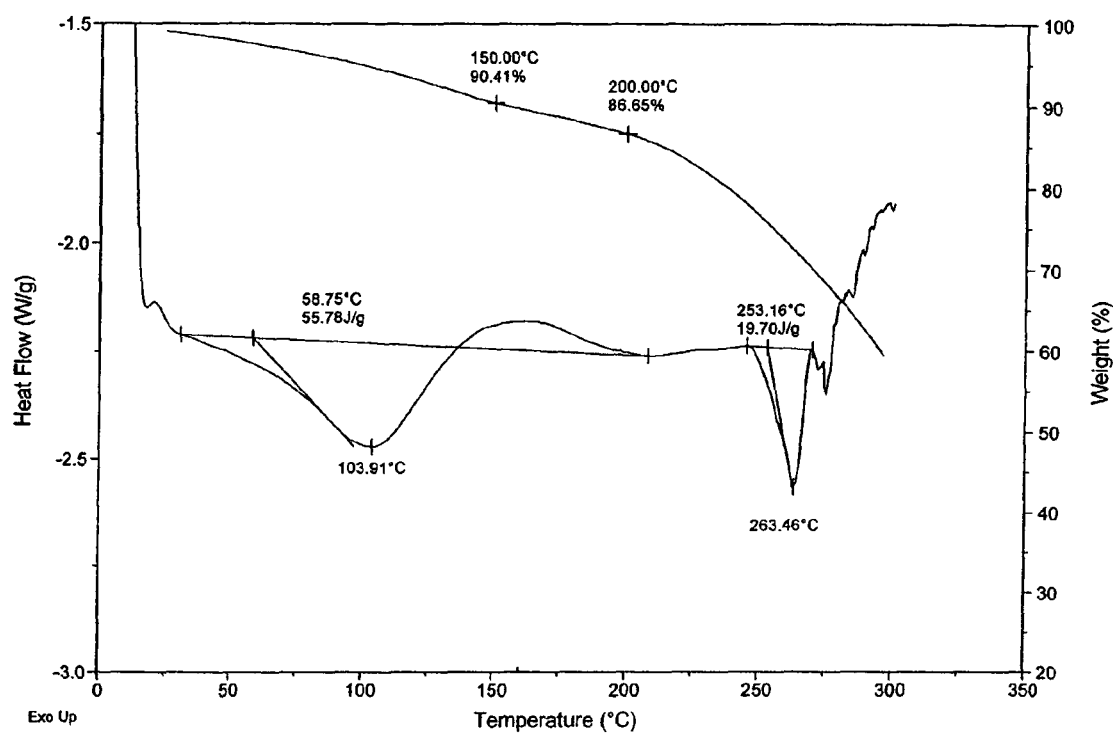
Figure 7:
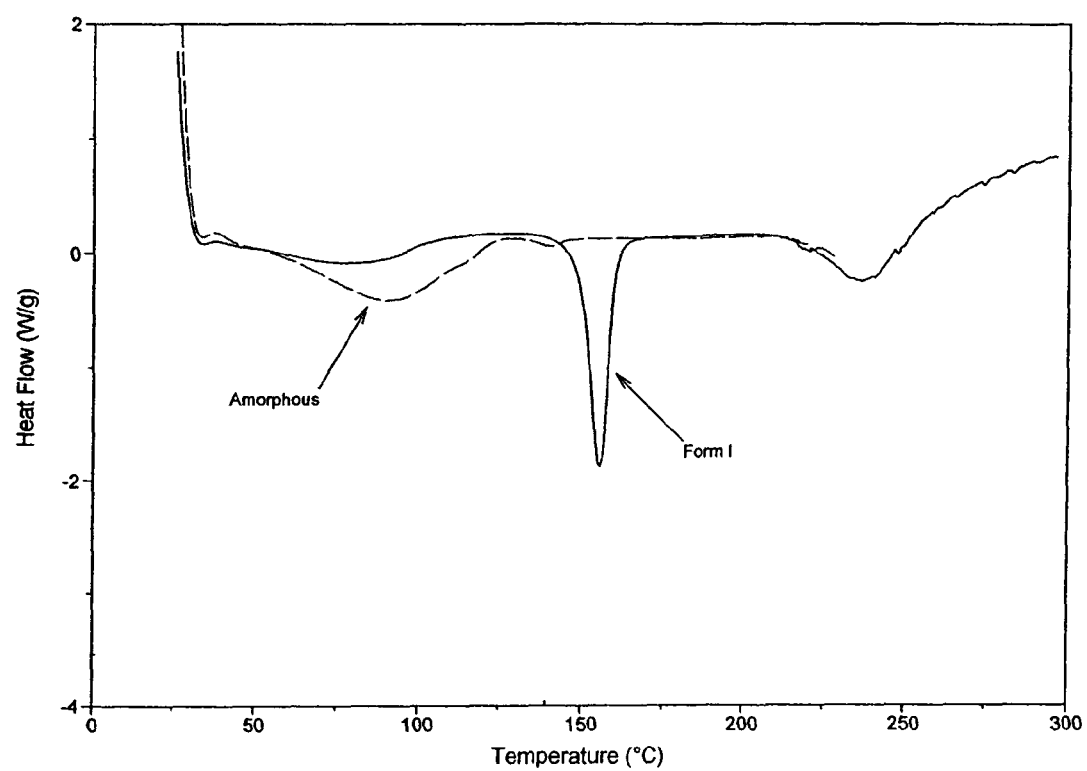
Figure 8:
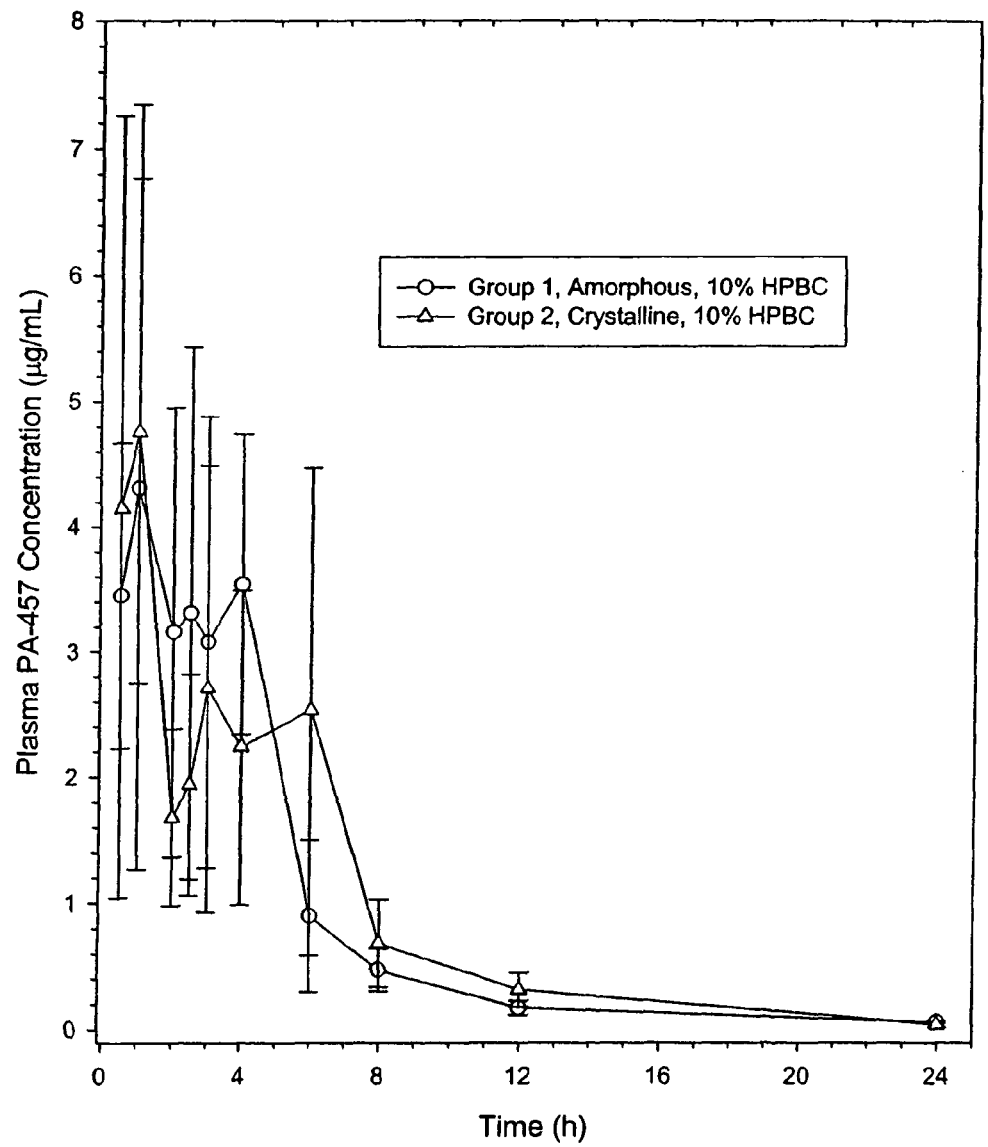
Figure 9:
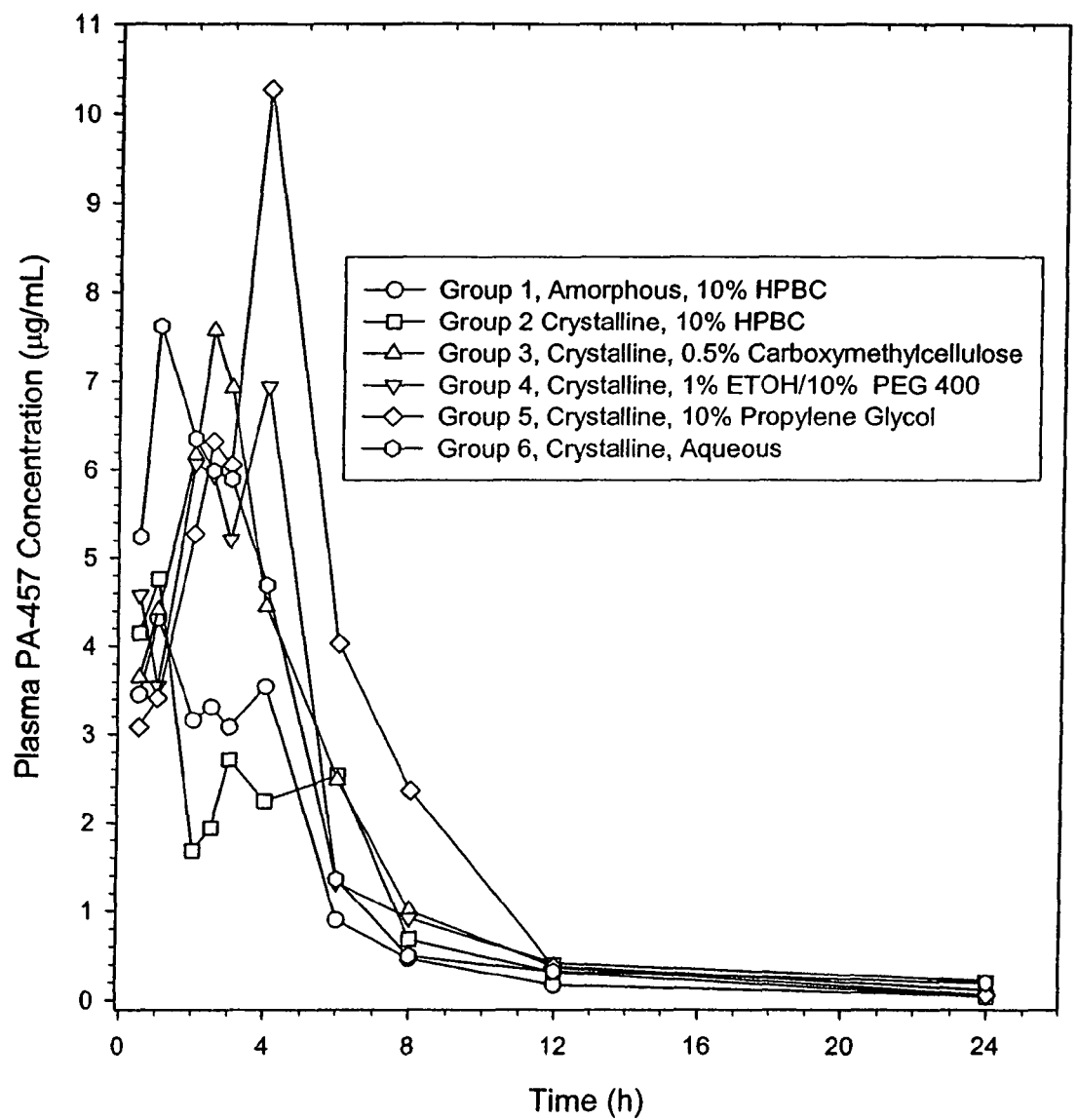
Figure 10:
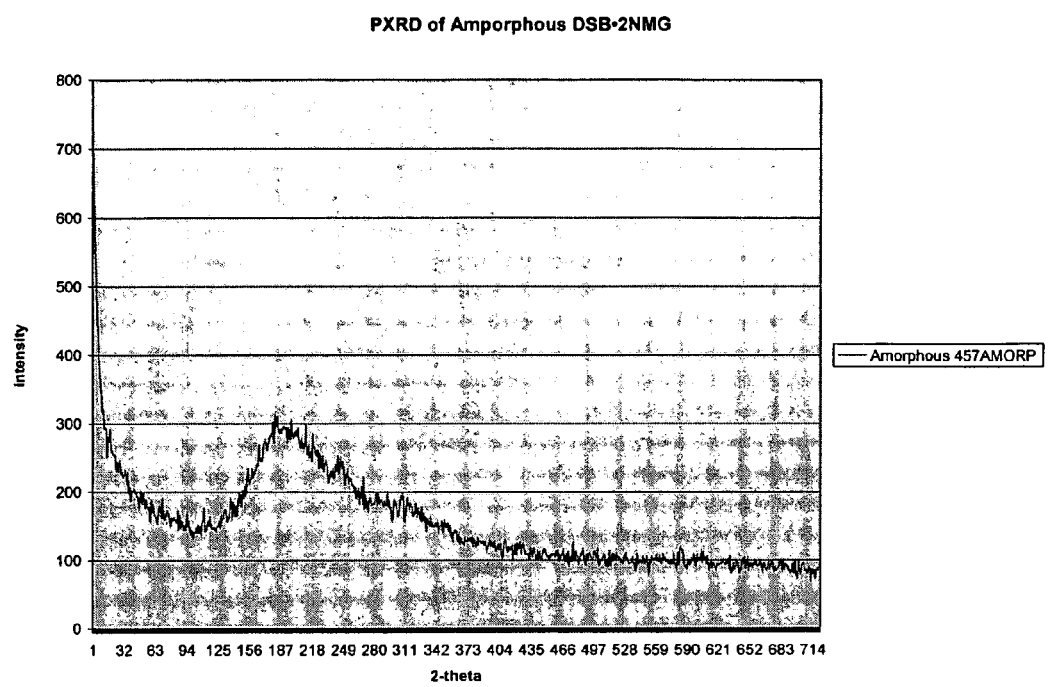

FIG. 1 is an X-ray Powder Diffraction (XRPD) pattern of DSB•2NMG Form I.
FIG. 2 is a Differential Scanning Calorimetry (DSC) thermogram of DSB•2NMG Form I.
FIG. 3 is a Thermogravimetric Analysis (TGA) and DSC overlay plot of DSB•2NMG Form I.
FIG. 4 is an XRPD pattern of DSB•2NMG Form I after annealing at 75° C. for 2 days.
FIG. 5 is an XRPD pattern of DSB•2NMG Form II.
FIG. 6 is a TGA and DSC overlay plot of DSB•2NMG Form II.
FIG. 7 is a DSC thermogram of amorphous DSB•2NMG overlayed with that of DSB•2NMG Form I.
FIG. 8 depicts the plasma concentration of DSB free acid versus time profile in rats administered a single 25 mg/mL oral dose of amorphous DSB•2NMG and DSB•2NMG Form I in aqueous 10% hydroxypropyl-β-cyclodextrin.
FIG. 9 depicts the plasma concentration of DSB free acid versus time profile in rats administered a single 25 mg/mL oral dose of amorphous DSB•2NMG and DSB•2NMG Form I in various solutions and suspensions.
FIG. 10 is an X-ray Powder Diffraction (XRPD) pattern of amorphous DSB•2NMG.

DETAILED DESCRIPTION OF THE INVENTION

Compounds of the present invention are useful in treating retroviral conditions, particularly HIV-related conditions.

As with all pharmaceutical compounds and compositions, chemical and physical properties of DSB•2NMG are important in its commercial development. These properties include, but are not limited to: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture, and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, processing and storage of pharmaceutical compositions comprising DSB•2NMG. Solid state forms of DSB•2NMG that provide an improvement in one or more of these properties relative to other solid state forms of DSB•2NMG are desirable.

According to the present invention, novel solid state forms of DSB•2NMG are provided. Specifically, these include crystalline forms (designated "Form I" and "Form II"). Also disclosed is an amorphous form of DSB•2NMG. Each solid state form of DSB•2NMG described in the present application possesses one or more of the above-described advantageous chemical or physical properties relative to other solid state forms of DSB•2NMG.

The term "amorphous" as applied to DSB•2NMG herein refers to a solid state form wherein the DSB•2NMG molecules are present in a disordered arrangement and do not form a distinguishable crystal lattice or unit cell. When subjected to X-ray powder diffraction, amorphous DSB•2NMG does not produce a diffraction pattern characteristic of a crystalline form.

The term "crystalline form" as applied to DSB•2NMG herein refers to a solid state form wherein the DSB•2NMG molecules are arranged to form a distinguishable crystal lattice (i) comprising distinguishable unit cells, and (ii) yielding diffraction peaks when subjected to X-ray radiation.

The term "DSB•2NMG drug substance" as used herein means DSB•2NMG per se as qualified by the context in which the term is used, and can refer to unformulated DSB•2NMG or to DSB•2NMG present as an ingredient of a pharmaceutical composition.

The term "phase pure" herein refers to purity with respect to other solid state forms of DSB•2NMG and does not necessarily imply a high degree of chemical purity with respect to other compounds.

As used herein in connection with a measured quantity, "about" refers to the normal variation in that measured quantity, as expected by the skilled artisan making the measurement and exercising a level of care commensurate with the objective of measurement and the precision of the measuring equipment. When used in relation with amount of time, "about" can have its ordinary meaning, and can be used to round the amount of time to simplify the language, for example, "about a few days" rather than "60 hours".

Preparation and Characterization

Many processes of the present invention involve crystallization out of a particular solvent. One skilled in the art would appreciate that the conditions concerning crystallization can be modified without affecting the form of the polymorph obtained. For example, when mixing DSB•2NMG in a first suitable solvent to form a solution, warming of the mixture can be necessary to completely dissolve the starting material. If warming does not clarify the mixture, the mixture can be diluted or filtered. To filter, the hot mixture can be passed through paper, glass fiber or other membrane material, or a clarifying agent such as Celite. Depending upon the equipment used and the concentration and temperature of the solution, the filtration apparatus may need to be preheated to avoid premature crystallization.

The conditions can also be changed to induce precipitation. A preferred way of inducing precipitation is to reduce the solubility of the first suitable solvent. The solubility of the solvent can be reduced, for example, by cooling the solvent.

In one embodiment, a second suitable solvent is added to a solution to decrease its solubility for a particular compound, thus resulting in precipitation. In another embodiment, a second suitable solvent is added to an oily residue or a gummy material, wherein the low solubility of the second suitable solvent for a particular compound results in precipitation of that compound.

In one embodiment, crystallization is accelerated is by seeding with a crystal of the product or scratching the inner surface of the crystallization vessel with a glass rod. In another embodiment, crystallization can occur spontaneously without any inducement. All that is necessary to be within the scope of the claims relating to processes of producing a DSB•2NMG polymorph is to form a precipitate or crystal.

DSB•2NMG Form I

In one aspect the present invention provides a process for preparing DSB•2NMG Form I comprising the steps of:
(a) preparing a solution of DSB•2NMG in a first suitable solvent;
(b) heating the solution to an elevated temperature;
(c) adjusting the temperature of the solution to a growth temperature;
(d) isolating crystalline DSB•2NMG Form I.

In some embodiments, the process for preparing DSB•2NMG Form I further comprises the step of introducing a second suitable solvent.

In some embodiments, the process for preparing DSB•2NMG Form I further comprises the step of seeding the resulting solvent system with a sample of DSB•2NMG Form I.

In some embodiments, saturated solutions are first prepared by agitating DSB•2NMG in contact with a first suitable solvent at the saturation temperature. The mother liquor is separated from any residual solids by filtration. The mother liquor is then diluted with a second suitable solvent, when necessary, and heated above the saturation temperature (overheated and unsaturated) of the resulting solvent system to dissolve any remaining solids. The temperature of the solution is then adjusted to the growth temperature, i.e., a temperature capable of allowing solidification of DSB•2NMG in the resulting solvent system.

DSB•2NMG Form I is prepared according the above-described process in solvent systems (approximate solubility in mg/mL, 25° C.) comprising one or more solvents such as methanol, ethanol (5), 1-propanol (5), 2-propanol (<3), 1-butanol (<3), 2-butanol (<3); dimethyl formamide (>50); acetone (<3), and the like.

In one embodiment, DSB•2NMG Form I is crystallized from a suitable solvent, such as, but not limited to, DMF, as exemplified below. In other embodiments, DSB•2NMG Form I is crystallized by techniques of solvent evaporation or solution saturation well known to those of ordinary skill in the art including but not limited to: introducing a shear flow; introducing a heated element such as heat transfer plates, infrared lamps, microwave systems; distillation with an optional sheer flow wherein the distillation can be performed at atmospheric pressure or under vacuum; static evaporation; reducing the temperature of the DSB•2NMG solution; and, thin film evaporation techniques such as rotary evaporation, spin-off evaporation, rising and falling film evaporation, submerged evaporation, and wiped film evaporation.

The XRPD pattern for DSB•2NMG Form I is shown in FIG. 1 and is characterized as having substantially the X-ray diffraction pattern shown in Table 1.

TABLE 1

X-Ray Diffraction Pattern for DSB.2NMG Form I

| 2-theta | I/I$_0$ (x100) |
| --- | --- |
| 4.43 | 100 |
| 5.74 | 43 |
| 8.91 | 20 |
| 11.32 | 87 |
| 11.88 | 33 |
| 12.17 | 14 |
| 12.64 | 21 |
| 13.23 | 29 |
| 13.72 | 33 |
| 15.33 | 31 |
| 15.89 | 11 |
| 16.42 | 27 |
| 16.72 | 27 |
| 17.32 | 27 |
| 18.57 | 14 |
| 19.01 | 15 |
| 19.40 | 16 |
| 19.80 | 30 |
| 20.26 | 25 |
| 21.02 | 5 |
| 21.79 | 6 |
| 22.50 | 8 |
| 23.85 | 9 |

The calorimetric features of DSB•2NMG Form I were investigated using Differential Scanning Calorimetry (DSC) as shown in FIG. 2. DSB•2NMG Form I undergoes three regions of thermal activity as shown by DSC. The first endothermic region is observed at approximately 50-110° C. and is consistent with solvent removal. The second thermal event has an extrapolated onset temperature of about 152° C. and an enthalpy of 86 J/g and is attributed to melting. The third region of thermal activity is observed at about 215° C. and is attributed to decomposition.

Thermogravimetric analysis (TGA) performed on DSB•2NMG Form I is shown in FIG. 3 along with its DSC curve. The TGA thermogram of DSB•2NMG Form I exhibits mass loss from ambient temperature until about 80° C., consistent with the loss of more than about 2% (w/w) volatiles (ethanol). The TGA temperature range for solvent removal is lower than observed in DSC (due to pressure build up in the DSC samples resulting from sample encapsulation). After solvent removal, the mass of the material is stable through melting and begins slowly losing mass above about 180° C. Above about 200° C., loss of mass becomes rapid. The TGA behavior is consistent with the thermal assignments observed using DSC.

DSB•2NMG Form I obtained by annealing at 75° C. for 2 days has substantially the XRPD pattern depicted in FIG. 4, and is characterized by diffraction signals at approximately 9.15, 12.90, and 17.80 degrees 2θ, in addition to the characteristic Form I pattern.

DSB•2NMG Form II

Following the general procedure described above, a new crystal form of DSB•2NMG was observed using methyl ethyl ketone (MEK) as the solvent system. This new crystal form is designated DSB•2NMG Form II and could be a MEK solvate.

The XRPD pattern for DSB•2NMG Form II is shown in FIG. 5 and is characterized as having substantially the X-ray diffraction pattern shown in Table 2.

TABLE 2

X-Ray Diffraction Pattern for DSB.2NMG Form II

| 2-theta | $I/I_0$ (x100) |
|---|---|
| 12.60 | 62 |
| 14.45 | 100 |
| 16.30 | 32 |
| 18.70 | 23 |
| 19.90 | 18 |
| 22.05 | 7 |
| 30.45 | 5 |
| 33.95 | 6 |

The DSC and TGA overlay thermogram for DSB•2NMG Form II is shown in FIG. 6. The DSC curve exhibits a broad desolvation endotherm from about 25° C. to about 130° C., while the corresponding TGA curve indicates the sample is about 9% (w/w) solvent. The calculated value for an MEK monosolvate is about 7% (w/w). Other thermal features of DSB•2NMG Form II include an exothermic signal from about 130° C. to about 200° C. which is accompanied by a second region of mass loss (TGA) and may be caused by decomposition. A third DSC signal is observed at about 253° C. and is consistent with decomposition.

Amorphous DSB•2NMG

Amorphous DSB•2NMG is prepared by dissolving DSB•2NMG in a solvent to form a solution of DSB•2NMG and either (a) adding an anti-solvent, i.e., a solvent in which DSB•2NMG is poorly soluble, or (b) spray drying the solution.

Preferably, the solvent is an alcohol, such as methanol, ethanol or isopropanol, or a ketone, such as acetone.

After dissolution of DSB•2NMG in the organic solvent, the organic solvent is removed under reduced or ambient pressure. The evaporation is preferably controlled, and one skilled in the art will appreciate that the conditions of evaporation can affect the quality of the product. The final product can optionally be triturated with an organic solvent such as a saturated hydrocarbon, including inter alia cyclohexane, hexane and heptane, or ethers, including inter alia MTBE (methyl tributyl ether).

The DSC thermogram for amorphous DSB•2NMG overlayed with that for DSB•2NMG Form I is shown in FIG. 7.

It is to be understood that each of DSB•2NMG Form I, DSB•2NMG Form II, and amorphous DSB•2NMG, in addition to having the XRPD, DSC, TGA and other characteristics described herein, may also possess other characteristics not described, such as but not limited to the presence of water or one or more solvent molecules.

In some embodiments of the present invention, the DSB•2NMG drug substance consists of substantially phase pure DSB•2NMG Form I.

In some embodiments of the present invention, the DSB•2NMG drug substance comprises at least about 90% DSB•2NMG Form I relative to all other solid state forms of DSB•2NMG present in the DSB•2NMG drug substance.

In some embodiments of the present invention, the DSB•2NMG drug substance comprises at least about 75% DSB•2NMG Form I relative to all other solid state forms of DSB•2NMG present in the DSB•2NMG drug substance.

In some embodiments of the present invention, the DSB•2NMG drug substance comprises at least a detectable amount of DSB•2NMG Form I relative to all other solid state forms of DSB•2NMG present in the DSB•2NMG drug substance.

In some embodiments of the present invention, the DSB•2NMG drug substance consists of substantially phase pure DSB•2NMG Form II.

In some embodiments of the present invention, the DSB•2NMG drug substance comprises at least about 90% DSB•2NMG Form II relative to all other solid state forms of DSB•2NMG present in the DSB•2NMG drug substance.

In some embodiments of the present invention, the DSB•2NMG drug substance comprises at least about 75% DSB•2NMG Form II relative to all other solid state forms of DSB•2NMG present in the DSB•2NMG drug substance.

In some embodiments of the present invention, the DSB•2NMG drug substance comprises at least a detectable amount of DSB•2NMG Form II relative to all other solid state forms of DSB•2NMG present in the DSB•2NMG drug substance.

Use and Administration

As a medicament, the presently described DSB•2NMG polymorphs are effective in the treatment of HIV and related disorders.

The present invention provides pharmaceutical compositions comprising: (i) at least one polymorph of the present invention, and (ii) at least one pharmaceutically acceptable excipient. In some embodiments of the present invention, the pharmaceutical composition comprises about 50% to about 99% by weight of a DSB•2NMG drug substance.

The present invention provides pharmaceutical compositions comprising: (i) at least one polymorph of the present invention, (ii) at least one pharmaceutically acceptable excipient, and (iii) at least one other anti-infective agent selected from the group consisting of anti-retrovirals, anti-HIV agents, immuno-stimulating compounds, antiviral antibodies, and fragments of antiviral antibodies. In some embodiments of the present invention, the pharmaceutical composition comprises about 50% to about 99% by weight of a DSB•2NMG drug substance.

By the term "anti-retroviral activity" or "anti-HIV activity" is intended the ability to inhibit at least one of:
  (1) viral pro-DNA integration into host cell genome;
  (2) retroviral attachment to cells;
  (3) viral entry into cells;
  (4) cellular metabolism which permits viral replication;
  (5) inhibition of intercellular spread of the virus;
  (6) synthesis or cellular expression of viral antigens;
  (7) viral budding or maturation;

(8) activity of virus-coded enzymes (such as reverse transcriptase, integrase and proteases); or (9) any known retroviral or HIV pathogenic actions, such as, for example, immunosuppression. Thus, any activity which tends to inhibit any of these mechanisms is "anti-retroviral activity" or "anti-HIV activity."

DSB•2NMG Form, I, DSB•2NMG Form II, and amorphous DSB•2NMG can be used for treatment of retroviral (e.g., HIV) infection either alone, or in combination with other modes of therapy known in the art. However, because DSB•2NMG Form I, DSB•2NMG Form II, and amorphous DSB•2NMG have pharmaceutically acceptable therapeutic windows, their utility is not limited to the treatment of established retroviral infections. For example, DSB•2NMG Form I, DSB•2NMG Form II, and amorphous DSB•2NMG can be used in treating blood products, such as those maintained in blood banks. The nation's blood supply is currently tested for antibodies to HIV. However, the test is still imperfect and samples which yield negative tests can still contain HIV virus. Treating the blood and blood products with DSB polymorphs of the present invention can add an extra margin of safety by inhibiting replication of any retrovirus that may have gone undetected.

Pharmaceutical compositions of the present invention can comprise at least one of DSB•2NMG Form I, DSB•2NMG Form II, and amorphous DSB•2NMG optionally in combination with one or more additional agent as described herein. Likewise, methods of treatment will employ pharmaceutical compositions that include at least one of DSB•2NMG Form I, DSB•2NMG Form II, and amorphous DSB•2NMG as described herein, alone or in combination with additional agents as further described. Such modes of therapy can include chemotherapy with at least one additional drug as presented herein.

In one embodiment, a pharmaceutical composition according to the present invention can comprise at least one other anti-viral agents such as, but not limited to, AZT (zidovudine, RETROVIR®, GlaxoSmithKline), 3TC (lamivudine, EPIVIR®, GlaxoSmithKline), AZT+3TC, (COMBIVIR®, GlaxoSmithKline), AZT+3TC+abacavir (TRIZIVIR®, GlaxoSmithKline), ddI (didanosine, VIDEX®, Bristol-Myers Squibb), ddC (zalcitabine, HIVID®, Hoffmann-La Roche), D4T (stavudine, ZERIT®, Bristol-Myers Squibb), tenofovir, abacavir (ZIAGEN®, GlaxoSmithKline), nevirapine (VIRAMUNE®, Boehringer Ingelheim), delavirdine (Pfizer), efavirenz (SUSTIVA®, DuPont Pharmaceuticals), saquinavir (INVIRASE®, FORTOVASE®, Hoffmann-LaRoche), ritonavir (NORVIR®, Abbott Laboratories), indinavir (CRIXIVAN®, Merck and Company), nelfinavir (VIRACEPT®, Pfizer), lopinavir, amprenavir (AGENERASE®, GlaxoSmithKline), adefovir (PREVEON®, HEPSERA®, Gilead Sciences), atazanavir (Bristol-Myers Squibb), fosamprenavir (LEXIVA®, GlaxoSmithKline) and hydroxyurea (HYDREA®, Bristol-Meyers Squibb), or any other antiretroviral drugs or antibodies in combination with each other, or associated with a biologically based therapeutic, such as, for example, gp41-derived peptides enfuvirtide (FUZEON®, Roche and Trimeris) and T-1249, or soluble CD4, antibodies to CD4, and conjugates of CD4 or anti-CD4, or as additionally presented herein.

Additional suitable antiviral agents for optimal use with at least one of DSB•2NMG Forms I and II and amorphous DSB•2NMG can include, but are not limited to amphotericin B (FUNGIZONE®); Ampligen (mismatched RNA) developed by Hemispherx Biopharma; BETASERON® (β-interferon, Chiron); butylated hydroxytoluene; Carrosyn (polymannoacetate); Castanospermine; Contracan (stearic acid derivative); Creme Pharmatex (containing benzalkonium chloride); 5-unsubstituted derivative of zidovudine; penciclovir (DENAVIR® Novartis); famciclovir (FAMVIR® Novartis); acyclovir (ZOVIRAX® GlaxoSmithKline); cytofovir (VISTIDE® Gilead); ganciclovir (CYTOVENE®, Hoffman LaRoche); dextran sulfate; D-penicillamine (3-mercapto-D-valine); FOSCARNET® (trisodium phosphonoformate; AstraZeneca); fusidic acid; glycyrrhizin (a constituent of licorice root); HPA-23 (ammonium-21-tungsto-9-antimonate); ORNIDYL® (eflomithine; Aventis); nonoxynol; pentamidine isethionate (PENTAM-300); Peptide T (octapeptide sequence, Peninsula Laboratories); Phenyloin (Pfizer); INH or isoniazid; ribavirin (VIRAZOLE®, Valeant Pharmaceuticals); rifabutin, ansamycin (MYCOBUTIN® Pfizer); CD4-IgG2 (Progenics Pharmaceuticals) or other CD4-containing or CD4-based molecules; Trimetrexate (Medimmune); suramin and analogues thereof (Bayer); and WELLFERON® α-interferon, GlaxoSmithKline).

DSB•2NMG drug substances can be used in the treatment of HIV in patients who are not adequately treated by other HIV-1 therapies. Accordingly, the invention is also drawn to a method of treating a patient in need of therapy, wherein the HIV-1 infecting said cells does not respond to other HIV-1 therapies. In another embodiment, methods of the invention are practiced on a subject infected with an HIV that is resistant to a drug used to treat HIV infection. In various applications, the HIV is resistant to one or more protease inhibitors, reverse transcriptase inhibitors, entry inhibitors, nucleoside analogs, vaccines, binding inhibitors, immunomodulators, or other inhibitors. In some embodiments, the compositions and methods of the invention are administered to a subject infected with an HIV that is resistant to one or more drugs used to treat HIV infections, for example, but not limited to, zidovudine, lamivudine, didanosine, zalcitabine, stavudine, abacavir, nevirapine, delavirdine, emtricitabine, efavirenz, saquinavir, ritonavir, lopinavir, indinavir, nelfinavir, tenofovir, amprenavir, adefovir, atazanavir, fosamprenavir, enfuvirtide, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflomithine, nonoxynol, pentamidine isethionate, peptide T, phenyloin, isoniazid, ribavirin, rifabutin, ansamycin, trimetrexate, SK-818, suramin, UA001, and combinations thereof.

In some embodiments of the present invention, DSB•2NMG drug substancescan be used as a prophylactic to prevent transmission of HIV infection between individuals. In other embodiments of the present invention, DSB•2NMG drug substances can be administered orally or by injection to an HIV infected pregnant woman or fetus during pregnancy or immediately prior to, at, or subsequent to birth, to reduce the probability that the newborn infant becomes infected. DSB•2NMG drug substances can be administered vaginally immediately prior to childbirth to prevent infection of the infant during passage through the birth canal. DSB•2NMG drug substances can be used during sexual intercourse to prevent transmission of HIV by applying a retroviral inhibiting effective amount of a topical composition including one or more salts of DSB to vaginal or other mucosa prior to sexual intercourse. In other embodiments of the present invention, DSB•2NMG drug substances can be used to prevent transmission of HIV from an infected male to an uninfected female or vice versa.

Pharmaceutical compositions of the present invention can also further comprise immunomodulators. In some embodiments of the present invention, the pharmaceutical composition comprises (i) a DSB•2NMG drug substance; (ii) an immunomodulator selected from the group consisting of ABPP (Bropririmine), Ampligen (mismatched RNA, Hemispherx Biopharma), anti-human interferon-α-antibody, ascorbic acid and derivatives thereof, interferon-β, Ciamexon, cyclosporine, cimetidine, CL-246,738, colony stimulating factors, including GM-CSF, dinitrochlorobenzene, HE2000 (Hollis-Eden Pharmaceuticals), inteferon-γ, glucan, hyperimmune gamma-globulin (Bayer), immuthiol (sodium diethylthiocarbamate), interleukin-1(Hoffmann-LaRoche; Amgen), interleukin-2 (IL-2) (Chiron), isoprinosine (inosine pranobex), Krestin, LC-9018 (Yakult), lentinan (Yamanouchi), LF-1695, methionine-enkephalin, Minophagen C, muramyl tripeptide (MTP-PE), naltrexone (Barr Laboratories), RNA immunomodulators, REMUNE® (Immune Response Corporation), RETICULOSE® (Advanced Viral Research Corporation), shosaikoto, ginseng, thymic humoral factor, Thymopentin, thymosin factor 5, thymosin 1 (ZADAXIN®, SciClone), thymostimulin, TNF (tumor necrosis factor) (Genentech), vitamin preparations, and combinations thereof.

Pharmaceutical compositions of the present invention can also further comprise anti-cancer therapeutic agents. Suitable anti-cancer therapeutic agents for optional use include an anti-cancer composition effective to inhibit neoplasia comprising a compound, or a pharmaceutically acceptable salt or prodrug of said anti-cancer agent, which can be used in combination therapy include, but are not limited to, alkylating agents, such as busulfan, cis-platin, mitomycin C, and carboplatin antimitotic agents, such as colchicine, vinblastine, taxols, such as paclitaxel (TAXOL®, Bristol-Meyers Squibb) docetaxel (TAXOTERE®, Aventis), topo I inhibitors, such as camptothecin, irinotecan and topotecan (HYCAMTIN®, GlaxoSmithKline), topo II inhibitors, such as doxorubicin, daunorubicin and etoposides such as VP16, RNA/DNA antimetabolites, such as 5-azacytidine, 5-fluorouracil and methotrexate, DNA antimetabolites, such as 5-fluoro-2'-deoxyuridine, ara-C, hydroxyurea, thioguanine, and antibodies, such as trastuzumab (HERCEPTIN®, Genentech), and rituximab (RITUXAN®, Genentech and Biogen-Idec), melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, alanosine, and combinations thereof.

The invention further provides methods for providing anti-bacterial therapeutics, anti-parasitic therapeutics, and anti-fungal therapeutics, for use in combination with DSB•2NMG Forms I and II and amorphous DSB•2NMG of the invention. Examples of anti-bacterial therapeutics include compounds such as penicillins, ampicillin, amoxicillin, cyclacillin, epicillin, methicillin, nafcillin, oxacillin, cloxacillin, dicloxacillin, flucloxacillin, carbenicillin, cephalexin, cepharadine, cefadoxil, cefaclor, cefoxitin, cefotaxime, ceftizoxime, cefinenoxine, ceftriaxone, moxalactam, imipenem, clavulanate, timentin, sulbactam, erythromycin, neomycin, gentamycin, streptomycin, metronidazole, chloramphenicol, clindamycin, lincomycin, quinolones, rifampin, sulfonamides, bacitracin, polymyxin B, vancomycin, doxycycline, methacycline, minocycline, tetracycline, amphotericin B, cyclosérine, ciprofloxacin, norfloxacin, isoniazid, ethambutol, and nalidixic acid, and combinations thereof.

Examples of anti-parasitic therapeutics include bithionol, diethylcarbamazine citrate, mebendazole, metrifonate, niclosamine, niridazole, oxamniquine and other quinine derivatives, piperazine citrate, praziquantel, pyrantel pamoate and thiabendazole, and combinations thereof.

Examples of anti-fungal therapeutics include amphotericin B, clotrimazole, econazole nitrate, flucytosine, griseofulvin, ketoconazole and miconazole, and combinations thereof. Anti-fungal compounds also include aculeacin A and papulocandin B.

A preferred animal subject of the present invention is a human being. In a particular embodiment, the present invention is useful in the treatment of human patients.

The term "treating" means the administration to a subject a DSB•2NMG drug substance according to the present invention for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

Pharmaceutical compositions for administration according to the present invention comprise a DSB•2NMG drug substance according to the present invention in a pharmaceutically acceptable form are optionally combined with a pharmaceutically acceptable carrier. These compositions can be administered by any means that achieve their intended purposes. Amounts and regimens for the administration of the solid state forms of DSB•2NMG according to the present invention can be determined readily by those with ordinary skill in the clinical art of treating a retroviral pathology.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one of DSB•2NMG Form I, DSB•2NMG Form II, and amorphous DSB•2NMG according to the present invention in an amount effective to achieve its intended purpose. While individual needs vary, determination of optimal ranges of effective amounts of each component is within the skill of the art. Typical dosages comprise about 0.1 to about 100 mg/kg body weight. A preferred dosage of one embodiment comprises about 1 to about 100 mg/kg body weight of the active ingredient. The dosages can comprise about 10 to about 100 mg/kg body weight. In another embodiment, the preferred dosage comprises about 1 to about 10 mg/kg body weight of the active ingredient.

Therapeutic administration can also include prior, concurrent, subsequent or adjunctive administration of at least one additional solid state form of DSB•2NMG according to the present invention or other therapeutic agent, such as an anti-viral or immune stimulating agent. In such an approach, the dosage of the second drug can be the same as or different from the dosage of the first therapeutic agent. In one embodiment of the present invention, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. In one embodiment, the preparations, particularly those preparations which can be administered orally, such as tablets, dragees, and capsules, and also preparations which can be administered rectally, such as suppositories, as well as suitable solutions for administration by injection or orally, contain from about 0.01 to 99 percent of the active ingredient together with the excipient. In another embodiment, the preparation can include from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Some embodiments further comprise a filler selected from the group consisting of saccharides, for example, lactose or sucrose, mannitol or sorbitol, cellulose preparations, calcium phosphates, such as tricalcium phosphate or calcium hydrogen phosphate, and combinations thereof.

Some embodiments further comprise a binder selected from the group consisting of starch paste, for example, maize starch, wheat starch, rice starch, potato starch, gelatin, tragacanth, methyl cellulose, hydroxypropylmethylcellulose, sodium carboxymethylcellulose, polyvinyl pyrrolidone (PVP), and combinations thereof.

Some embodiments further comprise a disintegrating agent selected from the group consisting of maize starch, wheat starch, rice starch, potato starch, gelatin, tragacanth, methyl cellulose, hydroxypropylmethylcellulose, sodium carboxymethylcellulose, polyvinyl pyrrolidone, carboxymethyl starch, cross-linked polyvinyl pyrrolidone, agar, alginic acid or a salt thereof, such as sodium alginate, and combinations thereof.

Some embodiments further comprise an auxiliary selected from the group consisting of flow-regulating agents and lubricants and combinations thereof. Some preferred auxiliaries are selected from the group consisting of silicas, talcs, stearic acids and salts and combinations thereof. Other preferred auxiliaries are selected from the group consisting of magnesium stearate calcium stearate, polyethylene glycol, and combinations thereof.

Some embodiments further comprise a dragee core optionally provided with a suitable coating which may provide a certain degree of resistance to gastric juices. For this purpose, concentrated saccharide solutions can be used, which can comprise gum arabics, talcs, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used.

Some embodiments further comprise a dyestuff or pigment which can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds can be dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as, for example, water or other solvents, solubilizing agents and emulsifiers such as ethyl alcohol, isopropyl alcohol, cyclodextrins such as hydroxypropyl-$\beta$-cyclodextrin, ethyl carbonate, ethyl acetate, benzyl alcohol, benzyl benzoate, propylene glycol, 1,3-butylene glycol, dimethyl formamide, oils such as cottonseed, groundnut, corn, germ, olive, castor, and sesame oils, glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, cellulose, microcrystalline cellulose, aluminum metahydroxide, bentonite, agar-agar, and tragacanth, and combinations thereof.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include oral dosage forms such as, but not limited to, hard or soft gelatin capsules, dragees, pills, tablets, including coated tables, elixirs, suspensions, syrups or inhalations and controlled release forms thereof.

Solid dosage forms in addition to those formulated for oral administration include rectal suppositories.

The solid state forms of DSB•2NMG of the present invention can also be administered in the form of an implant when compounded with a biodegradable slow-release carrier. Alternatively, the solid state forms of DSB•2NMG of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, the solid state forms of DSB•2NMG can be administered in the form of an infusion solution, a nasal inhalation or spray, or a mucosal or vaginal delivery system, such as a vaginal ring, foam, cream, gel, medicated suppository and medicated tampon.

Prophylactic topical compositions for preventing HIV infection between individuals during childbirth or sexual intercourse include one or more solid state forms of DSB•2NMG of the present invention and at least one pharmaceutically acceptable topical carrier or diluent. The topical composition can be, for example, in the form of an ointment, a cream, a gel, a lotion, a paste, a jelly, a spray, a foam, or a sponge. The dosage amount of a solid state form of DSB•2NMG in a prophylactic topical formulation is, in general, less than about 1,000 milligrams, and in some embodiments between about 0.01 to about 100 milligrams. The topical formulations can include other prophylactic ingredients. The carrier and diluents should be acceptable in the sense of being compatible with other ingredients of the formulation and not deleterious to the recipient.

Topical prophylactic formulations include those suitable for vaginal, rectal or topical administration. The formulations can, where appropriate, be conveniently presented in discrete dosage units, and can be prepared by any of the methods known in the art of pharmacy. All such methods include the step of bringing the active agent into association with liquid carriers, gels or finely divided solid carriers or both and then, if necessary, shaping the product into the desired formulation.

Prophylactic formulations suitable for vaginal administration can be presented as pessaries, tampons, creams, gels, pastes, jelly, foams, or sprays, or aqueous or oily suspensions, solutions or emulsions (liquid formulations) containing suitable carriers known in the art in addition to the active agent. Liquid formulations can contain conventional additives, such as, suspending agents, emulsifying agents, non-aqueous vehicles including edible oils, or preservatives. These formulations are useful to prevent both sexual transmission of HIV and infection of an infant during passage through the birth canal. In one example, the vaginal administration can take place prior to sexual intercourse, or immediately prior to childbirth.

In some embodiments, prophylactic formulations suitable for rectal or vaginal administration having a solid carrier are represented as unit dose suppositories. Suitable carriers include cocoa butter and other materials commonly used in the art. Suppositories can be formed, for example, mixing one or more solid state forms of DSB•2NMG with one or more softened or melted carriers followed by chilling and shaping in molds.

Prophylactic formulations according to the invention can also be in the form of drops formulated with an aqueous or non-aqueous base comprising one or more dispersing agents, solubilizing agents, or suspending agents. Liquid sprays can be delivered from pressurized packs.

Prophylactic formulations according to the invention can be adapted to give sustained delivery. Also, the prophylactic formulations can include other active agents, such as spermicidal agents, antimicrobial agents, and anti-viral agents.

DSB•2NMG Form I, DSB•2NMG II, and amorphous DSB•2NMG can also be administered in the form of an implant when compounded with a biodegradable slow-release carrier. Alternatively, the triterpene derivatives of the present invention can be formulated as a transdermal patch for continuous release of the active ingredient.

The free acid of DSB can be obtained by the synthesis method described in U.S. Pat. No. 5,679,828, herein incorporated by reference in its entirety.

Analytical Characterization

The following describes the instrumentation used by the present invention to characterize the new polymorphs. XRPD patterns were obtained by methods known in the art using a Scintag XDS2000 θ/θ X-ray powder diffractometer operating with Cu Kα radiation and using a Kevex Psi Peltier-cooled solid state detector. The source slits of 2 and 4 mm and detector slits of 0.5 and 0.3 mm were used for data collection. A milled sample was placed in a stainless steel sample holder and leveled. The XRPD pattern of the sample was obtained from 2° to 42° 2θ at a 1°/min-scan rate. Calibration of the diffractometer is verified annually using a silicon powder standard.

The DSC thermogram was obtained using a Perkin Elmer Pyris 1 DSC equipped with an Intracooler 2P-refrigeration unit. The Pyris 1 was purged with nitrogen. Calibration was performed prior to analysis using an Indium standard at 10° C./min-heating rate. Approximately 2 mg of the sample was sealed in a PerkinElmer 20 µL universal aluminum pan with holes in the lid. The sample was heated from room temperature to 300° C. at 10° C./min.

The DTG Profile for TGA analysis was obtained by a Perkin Elmer TGA 7 purged with nitrogen. A 100 mg standard weight and a nickel sample were used to verify balance and temperature calibrations, respectively. The sample was heated from room temperature to 350° C. at 10° C./min.

EXAMPLES

DSB•2NMG Form I 20 gDSB and 13.49 g (2.02 eq.) N-methyl-D-glucamine are dissolved in 70 mL methanol at 50-60° C. in vessel A. The clear solution is filtered into vessel B. Vessel A and the filter funnel are washed with methanol into vessel B. The clear solution is stirred slowly, cooled to room temperature and seeded. Within 1 h a thick suspension is formed. The agitation is increased before adding ethanol at room temperature. The suspension is heated to 60° C. (oil bath) for 10 min and is then cooled slowly to room temperature. The crystals are filtered and dried at 50° C. in vacuo overnight. Yield: 31.6 g (94

DSB•2NMG Form I is also prepared by a process in which 50 mg DSB•2NMG is dissolved in 1 mL DMF and stirred overnight at 25° C. overnight. The resulting clear, colorless solution is filtered through a 0.2 micron PTFE filter and heated to 35° C. for one hour. The solution temperature is adjusted to 25° C. and a nitrogen shear is introduced at 3 psi to evaporate the solution. The resulting crystals are dried.

DSB•2NMG Form II

A saturated solution of DSB•2NMG in methyl ethyl ketone (MEK) is prepared by agitating approximately 50 mg of Form I DSB-2NMG with MEK at 25° C. The mother liquor is separated from any residual solids by filtration. The mother liquor is then heated to 35° C. to dissolve any remaining solids or nuclei. The temperature of the solution is then adjusted to 25° C. and a nitrogen shear flow of 3-5 psig is introduced to evaporate the solvent. Crystals of Form II are produced.

Amorphous DSB•2NMG

N-methyl-D-glucamine (2,097.40 mg) is dissolved in 250 mL methanol. DSB is added and while sitting overnight, the suspension becomes a solution. The solvent is removed with a nitrogen gas stream while externally heating to 40-60° C. with a water bath to form a thick, colorless oil. 200 mL methanol is added to dissolve the oil. Slow addition of 200 mL diethyl ether to the swirling mixture affords a white solid. Isolation of the solid material by vacuum filtration affords 5.52 g solids. Drying of the solids for 72 hours under vacuum affords 4.97 g amorphous DSB•2NMG.

Comparative Example

The following study was conducted to compare the relative bioavailability of oral formulations prepared with DSB•2NMG Form I and amorphous DSB•2NMG.

Groups of four male Sprague Dawley rats with surgically implanted jugular cannulas were given a single oral 25 mg/kg dose of DSB•2NMG (Form I or amorphous) in one of six formulations:

Group 1: 10% hydroxypropyl-β-cyclodextrin solution of amorphous DSB•2NMG;

Group 2: 10% hydroxypropyl-β-cyclodextrin solution of DSB•2NMG Form I;

Group 3: Suspension of DSB•2NMG Form I in 0.5% carboxymethylcellulose;

Group 4: Solution of DSB•2NMG Form I in 1% ethanol/10% polyethylene glycol 400/89% water;

Group 5: Solution of DSB•2NMG Form I in 10% propylene glycol/90% water; and

Group 6: Solution of DSB•2NMG Form I in water.

Serial blood samples were collected at scheduled times through 24 hours postdose and concentrations of DSB as the free acid in plasma were determined. Plasma concentrations of DSB as the free acid were measured in most animals for 24 hours after each dose.

When compared to formulations of amorphous DSB•2NMG, the hydroxypropyl-α-cyclodextrin formulation of DSB•2NMG Form I produced equivalent plasma concentration profiles, as shown in FIG. 8. Maximum observed concentration ($C_{max}$) averaged 5.46-5.27 µg/mL and occurred approximately 2 hours after the dose. The area under the plasma concentration-time curve from time zero extrapolated to infinity ($AUC_{INF}$) were similar and averaged 21.51 µg h/mL and 23.44 µg h/mL after doses of the amorphous and Form I DSB•2NMG, respectively. Half-lives of DSB free acid averaged 4.57 h-4.04 h from the hydroxypropyl-β-cyclodextrin formulations.

For formulations of DSB•2NMG Form I, the greatest exposure to DSB free acid was observed with the 10% propylene glycol/water vehicle, as shown in FIG. 9. DSB free acid concentrations after doses of DSB•2NMG Form I formulated in 0.5% carboxymethylcellulose, 1% ethanol/10% polyethylene glycol 400/water, 10% propylene glycol/water, and in water were also greater than those observed after administration of DSB•2NMG Form I given in 10% hydroxypropyl-β-cyclodextrin. $C_{max}$ averaged 8.20, 8.49, 10.45, and 9.77 µg/mL, for each formulation respectively and occurred at means of 1.38 h after the dose. The $AUC_{INF}$ observed were approximately 1.5-2 times greater than from DSB•2NMG Form I given in hydroxypropyl-β-cyclodextrin.

What is claimed is:

1. A crystalline form of 3-O-(3',3'-dimethylsuccinyl)betulinic acid di-N-methyl-D-glucamine (DSB•2NMG) having substantially the following X-ray powder diffraction pattern obtained with copper irradiation:

| 2-theta | $I/I_0$ (x100) |
|---|---|
| 4.43 | 100 |
| 5.74 | 43 |
| 8.91 | 20 |
| 11.32 | 87 |
| 11.88 | 33 |
| 12.17 | 14 |
| 12.64 | 21 |
| 13.23 | 29 |
| 13.72 | 33 |
| 15.33 | 31 |
| 15.89 | 11 |
| 16.42 | 27 |
| 16.72 | 27 |
| 17.32 | 27 |
| 18.57 | 14 |
| 19.01 | 15 |
| 19.40 | 16 |
| 19.80 | 30 |
| 20.26 | 25 |
| 21.02 | 5 |
| 21.79 | 6 |
| 22.50 | 8 |
| 23.85 | 9. |

2. The crystalline form of DSB•2NMG according to claim 1, wherein the crystalline form contains less than about 25% of other solid forms of DSB•2NMG.

3. The crystalline form of DSB•2NMG according to claim 1, wherein the crystalline form contains less than about 10% of other solid forms of DSB•2NMG.

4. The crystalline form of DSB•2NMG according to claim 1, wherein the crystalline form is substantially phase pure.

5. The crystalline form of DSB•2NMG according to claim 1, and further characterized by a Differential Scanning Calorimetry profile with an endotherm at about 152° C.

6. A process for preparing the crystalline form of DSB•2NMG of claim 1 comprising the steps of:
 (a) preparing a saturated solution of DSB•2NMG in methanol;
 (b) heating the solution above the saturation temperature to completely dissolve the DSB•2NMG;
 (c) adjusting the temperature of the solution to a growth temperature; and,
 (d) isolating the crystalline form of DSB•2NMG of claim 1.

7. The process of claim 6 further comprising the step of introducing ethanol prior to heating the solution to an elevated temperature to completely dissolve the DSB•2NMG.

8. The process of claim 6 further comprising the step of seeding the solution of step (c) with a crystal of the crystalline form of DSB•2NMG of claim 1.

9. The process of claim 6, wherein the heated solution of step (b) is filtered prior to step (c).

10. A solid pharmaceutical composition comprising the crystalline form of DSB•2NMG according to claim 1, and a pharmaceutically-acceptable carrier.

11. A method of treating a retroviral infection, comprising administering to patient in need thereof an effective amount of the crystalline form of DSB•2NMG according to claim 1.

12. A drug substance comprising at least a detectable amount of the crystalline form of DSB•2NMG according to claim 1.

13. A drug substance comprising about 90% to about 100% of the crystalline form of DSB2•NMG according to claim 1.

14. A drug substance comprising substantially phase pure crystalline DSB•2NMG according to claim 1.

15. The drug substance of claim 13 wherein the balance of the DSB•2NMG consists of one or more of (i) other crystalline forms of DSB•2NMG, (ii) a solvated crystalline form of DSB•2NMG and (iii) amorphous solid DSB•2NMG.

16. A crystalline form of DSB•2NMG characterized by an X-ray powder diffraction pattern substantially as depicted in FIG. 4, and prepared by annealing the crystalline form of DSB•2NMG of claim 1.

17. A crystalline form of 3-O-(3',3'-dimethylsuccinyl) betulinic acid di-N-methyl-D-glucamine (DSB•2NMG) having substantially the following x-ray powder diffraction pattern obtained with copper irradiation:

| 2-theta | $I/I_0$ (x100) |
|---------|----------------|
| 12.60   | 62             |
| 14.45   | 100            |
| 16.30   | 32             |
| 18.70   | 23             |
| 19.90   | 18             |
| 22.05   | 7              |
| 30.45   | 5              |
| 33.95   | 6.             |

18. A process for preparing the crystalline form of DSB•2NMG of claim 17, comprising the steps of:
(a) preparing a saturated solution of DSB•2NMG in methyl ethyl ketone;
(b) heating said solution above the saturation temperature to completely dissolved the DSB•2NMG;
(c) adjusting the temperature of said solution to a growth temperature;
(d) evaporating the solvent; and, (e) isolating the crystalline form of DSB•2NMG of claim 17.

19. The process of claim 18 further comprising the step of seeding the solution of step (c) with a crystal of the crystalline form of DSB•2NMG of claim 17.

20. The process of claim 18, wherein the heated solution of step (b) is filtered prior to step (c).

21. A solid pharmaceutical composition comprising the crystalline form of DSB•2NMG according to claim 16, and a pharmaceutically-acceptable carrier.

22. A method of treating a retroviral infection, comprising administering to patient in need thereof an effective amount of the crystalline form of DSB•2NMG according to claim 16.

23. A drug substance comprising at least a detectable amount of the crystalline form of DSB•2NMG according to claim 16.

24. A drug substance comprising about 90% to about 100% of the crystalline form of DSB•2NMG according to claim 16.

25. A drug substance comprising substantially phase pure crystalline DSB•2NMG according to claim 16.

26. The drug substance of claim 24 wherein the balance of the DSB•2NMG consists of one or more of (i) other crystalline forms of DSB•2NMG, (ii) a solvated crystalline form of DSB•2NMG and (iii) amorphous solid DSB•2NMG.

27. A process of preparing the crystalline form of DSB•2NMG characterized by an X-ray powder diffraction pattern substantially as depicted in FIG. 4, comprising the steps provided in claim 6, and further comprising the step of annealing the isolated crystalline form of DSB•2NMG.

28. The process of claim 27, wherein said annealing step comprises annealing at about 75° C. for about 2 days.

* * * * *